US00PP27885P3

(12) United States Plant Patent
Merz

(10) Patent No.: US PP27,885 P3
(45) Date of Patent: Apr. 11, 2017

(54) ***GERANIUM* PLANT NAMED 'BOO'**

(50) Latin Name: *Geranium hybrida*
Varietal Denomination: Boo

(71) Applicant: Michael Merz, Offenbach (DE)

(72) Inventor: Michael Merz, Offenbach (DE)

( * ) Notice: Subject to any disclaimer, the term of this patent is extended or adjusted under 35 U.S.C. 154(b) by 56 days.

(21) Appl. No.: 14/545,139

(22) Filed: Mar. 30, 2015

(65) Prior Publication Data

US 2016/0295774 P1 Oct. 6, 2016

(51) Int. Cl.
*A01H 5/02* (2006.01)

(52) U.S. Cl.
USPC ..... Plt./324

(58) Field of Classification Search
USPC ..... Plt./324
See application file for complete search history.

(56) References Cited

PUBLICATIONS http://www.daytonnursery.com/encyclopedia/perennials/geranium.htm , Dayton Nursery, Cranesbill Geraniums, downloaded Jul. 22, 2016.*

* cited by examiner

*Primary Examiner* — Anne Grunberg

(57) ABSTRACT

A new cultivar of *Geranium* plant named 'Boo' that is characterized by large mauve-pink flowers with dark purple veins and whitish centers, a long flowering season and vigorous growth.

1 Drawing Sheet

Botanical classification: *Geranium hybrida.*
Variety denomination: 'Boo'.

BACKGROUND OF THE INVENTION

The present invention relates to a new and distinct cultivar of *Geranium* plant botanically known as *Geranium hybrida* and hereinafter referred to by the cultivar name 'Boo'.

'Boo' was discovered in the summer of 2010 as a chance seeding in a commercial crop of *Geranium* 'Jolly Bee' (U.S. Plant Pat. No. 12,148). The pollen parent plant is unknown. The cultivar 'Boo' was selected by the inventor as a single plant in a cultivated area of Offenbach, Germany.

Asexual propagation of the new cultivar 'Boo' first occurred by division in the spring of 2011 in Offenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Geranium* cultivar 'Boo'. These traits in combination distinguish 'Boo' as a new and distinct cultivar apart from other existing known varieties of *Geranium.*

1. *Geranium* 'Boo' exhibits large mauve-pink flowers with dark purple veins and whitish centers.
2. *Geranium* 'Boo' exhibits a long flowering season.
3. *Geranium* 'Boo' exhibits vigorous growth.

The closest comparison cultivar is the female parent plant *Geranium* 'Jolly Bee'. 'Boo' is distinguishable from 'Jolly Bee' by the following characteristics:

1. 'Boo' exhibits mauve-pink flowers with dark purple veins and whitish center. In contrast, 'Jolly Bee' has azure-blue flowers with whitish centers and dark-purple veins.

2. 'Boo' exhibits flower petals that are narrower and have less overlap than those of 'Jolly Bee'.
3. 'Boo' exhibits foliage that has wider lobes with shallower indentations than 'Jolly Bee',

*Geranium* 'Boo' can be compared to the *Geranium* cultivars 'Ballerina', 'Claridge Druce', 'Confetti' and 'Dreamland'. 'Ballerina' has a more compact, mounding habit and smaller foliage than 'Boo'. 'Ballerina' has smaller flowers that are lighter lilac-pink in color than 'Boo'. The petal base of 'Ballerina' is dark purple with ventricose veins. In contrast, the petal base of 'Boo' is almost white with linear veins. 'Ballerina' flowers mainly in late spring and early summer. In contrast, 'Boo' flowers late spring in October. 'Claridge Druce' has smaller flowers that are paler pink in color than 'Boo'. 'Confetti' has a smaller overall size and smaller flowers than 'Boo'. 'Confetti' has pale lilac flowers with purple venation and a darker petal base. The leaves of 'Confetti' exhibit creamy-white variegation. In comparison, the leaves of 'Boo' are solid green. The flowers of 'Dreamland' are lighter pink in color than the flowers of 'Boo'. In comparison, the flowers of 'Boo' are darker pink in color with an almost white petal base.

BRIEF DESCRIPTION OF THE DRAWING

The accompanying photograph illustrates the distinguishing traits of *Geranium* 'Boo'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Geranium* cultivar named 'Boo'. Data was collected in Offenbach, Germany from 12 month old outdoor grown plants in 20 cm. diameter containers. The time of year was Autumn and the temperature range was 15-28 degrees Centigrade during the day and 8-15 degrees Centigrade at night. No growth retardants were used. Color determinations are in accordance with The Royal Horticultural Society Colour Chart 2007 edition, except where general color terms of ordinary dictionary significance are used. The growing requirements are similar to the species. 'Boo' has not been tested under all possible conditions and phenotypic differences may be observed with variations in environmental, climatic, and cultural conditions, however, without any variance in genotype.

Botanical classification: *Geranium hybrida 'Boo'*.

Annual or perennial: Perennial.

Parentage: Seed parent plant: 'Jolly Bee'. The pollen parent plant is unknown.

Vigor: Strong.

Growth habit: Spreading.

Plant shape: Mounding.

Suitable container size: 20 cm.

Overall plant dimensions: 45 cm. in height and 70 cm. in diameter.

Low temperature tolerance: −20° Centigrade.

High temperature tolerance: 35° Centigrade.

Propagation: Terminal cuttings.

Time to initiate roots in summer: 15 days to initiate roots at 25° Centigrade.

Time to initiate roots in winter: 18 days to initiate roots at 20° Centigrade.

Time to produce a rooted cutting or liner in summer: 20 days at 25° Centigrade.

Time to produce a rooted cutting or liner in winter: 25 days at 20° Centigrade.

Crop time: Approximately 22 weeks.

Root system: Fine and fibrous.

Stem:

*Branching habit.*—Freely branching.
*Basal branching.*—Yes.
*Average number of lateral branches.*—20.
*Pinching.*—No.
*Lateral branch dimensions.*—2.5 mm. in diameter and 47 cm. in length.
*Internode length.*—12 cm.
*Stem texture.*—Smooth.
*Stem strength.*—Moderate.
*Stem color.*—144C.
*Pubescence.*—Absent.

Foliage:

*Leaf arrangement.*—Alternate.
*Compound or single.*—Single.
*Number of leaves per lateral branch.*—40.
*Leaf shape.*—Palmately divided.
*Leaf apex.*—Acute.
*Leaf base.*—Sagittate.
*Leaf dimensions.*—9 cm. in length and 10 cm. in width.
*Texture.*—Short hairs on both surfaces.
*Leaf margin.*—Dentate.
*Venation pattern.*—Palmate.
*Young leaf color* (*upper surface*).—146A.
*Young leaf color* (*lower surface*).—138B.
*Mature leaf color* (*upper surface*).—147A.
*Mature leaf color* (*lower surface*).—138B.
*Vein color* (*upper surface*).—138C.
*Vein color* (*lower surface*).—138C.
*Petiole dimensions.*—10 cm. in length and 2 mm. in diameter.
*Petiole color.*—144C.
*Durability of foliage to stress.*—Moderate.

Flower:

*Inflorescence arrangement.*—Axillary racemes.
*Inflorescence dimensions.*—12 cm. in height and 10 cm. in width.
*Quantity of flowers per inflorescence.*—2 to 3.
*Quantity of flowers per lateral stem.*—5 to 7.
*Quantity of flower buds per lateral stem.*—7 to 9.
*Quantity of flowers and buds per plant.*—20 to 25.
*Natural flowering season.*—July to October.
*Rate of flower opening.*—Every 2 to 3 days.
*Fragrance.*—None.
*Flower bud length.*—10 mm.
*Flower bud diameter.*—0.4 mm. in diameter.
*Flower bud shape.*—Ovoid.
*Bud color.*—138B.
*Rate of bud opening.*—2 to 3 days.
*Flower aspect.*—Outward/upright.
*Flower shape.*—Rotate.
*Flower dimensions.*—4.5 cm. in diameter and 1.5 cm. in height.
*Flower longevity.*—3 to 4 days.
*Number of petals.*—5.
*Fused or unfused.*—Unfused.
*Petal arrangement.*—Rotate.
*Petal shape.*—Obcordate.
*Petal texture.*—Smooth on both surfaces.
*Petal margin.*—Entire.
*Petal apex.*—Obcordate.
*Petal base.*—Attenuate.
*Petal dimensions.*—2.3 cm. in length and 1.8 cm in width.
*Petal color when opening* (*upper side*).—N80A, base 85D, veins 83B.
*Petal color when opening* (*under side*).—N78C.
*Petal color fully opened* (*upper side*).—N80A, base 85D, veins 83B.
*Petal color fully opened* (*under side*).—N78C.
*Petal color fading to.*—N78C.
*Self-cleaning or persistent.*—Self-cleaning.

Calyx:

*Calyx dimensions.*—1.3 cm. in length and 2 cm. in diameter.

Sepals:

*Sepal arrangement.*—Rotate.
*Number of sepals.*—5.
*Sepal shape.*—Oval.
*Sepal margin.*—Entire.
*Sepal apex.*—Acuminate.
*Sepal base.*—Attenuate.
*Sepal dimensions.*—1.3 cm. in length and 0.6 cm. in width.
*Young sepal color* (*upper side*).—144D.
*Young sepal color* (*under side*).—144B.
*Mature sepal color* (*upper side*).—144D.
*Mature sepal color* (*under side*).—144B.

Peduncle:

*Peduncle dimensions.*—8 cm. in length and 2 mm. in diameter.
*Pedicel angle.*—Upright to 40 degrees from stem.
*Peduncle strength.*—Weak.
*Peduncle color.*—144D.

Pedicels:

*Pedicel dimensions.*—5 cm. in length and 1.5 mm. in diameter.

*Pedicel strength.*—Weak.

*Pedicel color.*—144D.

Reproduction organs:

*Stamen number.*—10.

*Anther shape.*—Oblong.

*Anther size.*—1.5 mm in length.

*Anther color.*—79A.

*Amount of pollen.*—Low.

*Pollen color.*—79A.

*Pistil number.*—5.

*Pistil length.*—1.5 mm.

*Stigma shape.*—Linear.

*Stigma color.*—71B.

*Style length.*—3.5 mm.

*Style color.*—79A.

*Ovary color.*—144D.

Fruit and seed: Fruit and seed production have not been observed.

Disease and pest resistance: Disease and pest resistance have not been observed.

The invention claimed is:

1. A new and distinct variety of *Geranium* plant named 'Boo' as described and illustrated.

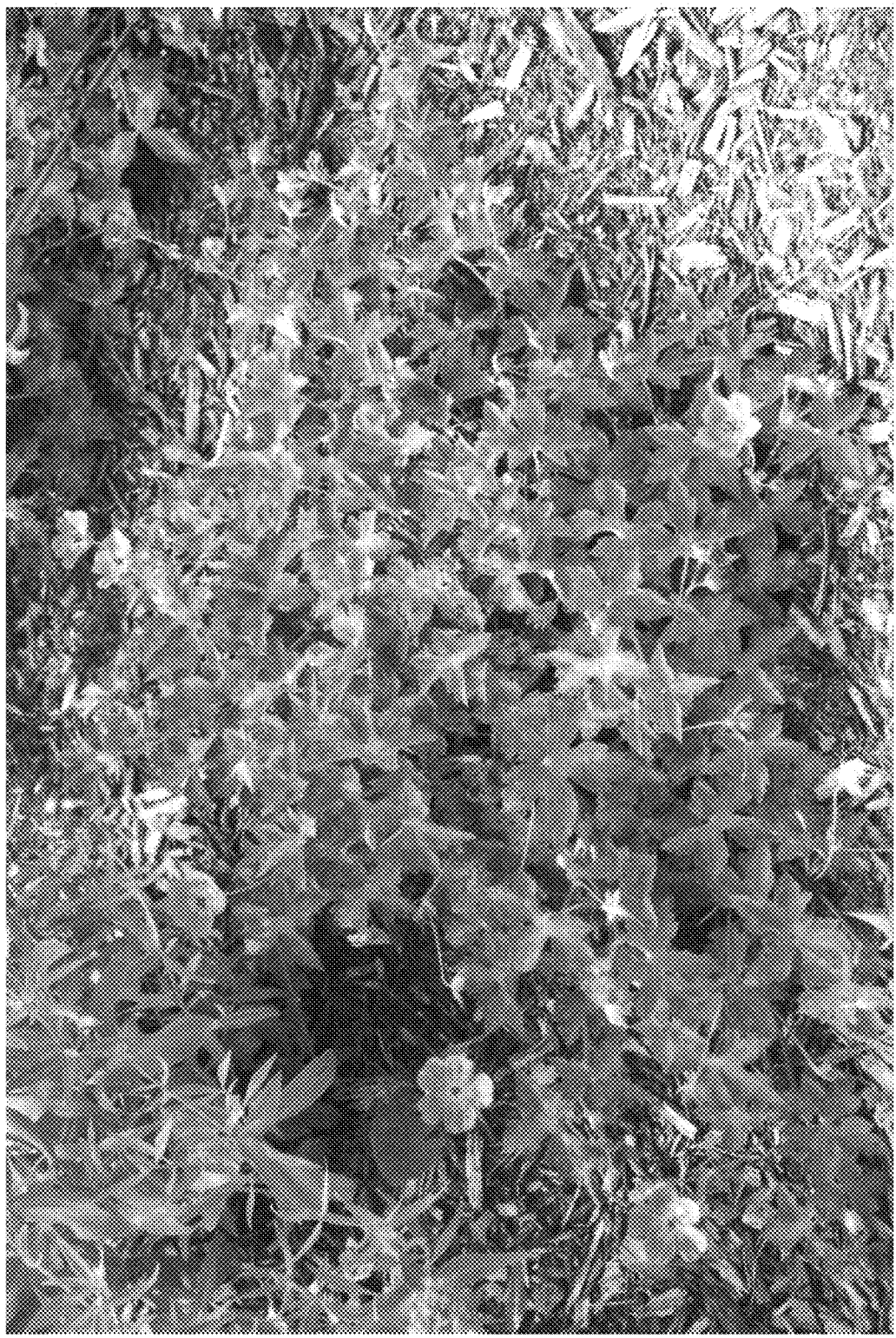

* * * * *